United States Patent [19]

Oystese

[11] 4,096,246

[45] Jun. 20, 1978

[54] ZINC BACITRACIN COMPOSITION FOR USE AS A FEED SUPPLEMENT AND METHOD FOR MAKING THE SAME

[75] Inventor: Brigt Oystese, Haslum, Norway

[73] Assignee: A/S Apothekernes Laboratorium for Specialpraeparater, Oslo, Norway

[21] Appl. No.: 730,092

[22] Filed: Oct. 6, 1976

[51] Int. Cl.² .............................................. A61K 37/00
[52] U.S. Cl. .................................................... 424/177
[58] Field of Search ......................................... 424/177

[56] References Cited

U.S. PATENT DOCUMENTS

| | | | |
|---|---|---|---|
| 2,809,892 | 10/1957 | Chornock | 424/177 |
| 3,116,207 | 12/1963 | Malinos | 424/177 |

*Primary Examiner*—Elbert L. Roberts

*Attorney, Agent, or Firm*—Seidel, Gonda & Goldhammer

[57] ABSTRACT

A zinc bacitracin composition for use as a feed supplement which possesses improved stability to heat, mechanical mixing and moisture when used in substantially dry animal feeds. Zinc bacitracin is precipitated by the addition of zinc cations, as in the range of between 0.5 to 0.7 g $Zn^{++}$/g bacitracin to a bacitracin fermentation broth, and then concentrated to 25 to 35% dry matter. Finely divided carrier material, such as calcium carbonate, is then added to the extent of 50 to 100 weight percent based on the dry matter, and the mixture is agitated to get a uniform mix. The uniform mixture is then spray dried to produce substantially spherical particles of the zinc bacitracin composition.

16 Claims, No Drawings

ZINC BACITRACIN COMPOSITION FOR USE AS A FEED SUPPLEMENT AND METHOD FOR MAKING THE SAME

My invention relates to a zinc bacitracin composition for use as a feed supplement, and to a method for making the same. The zinc bacitracin composition of my invention possesses increased stability when admixed with animal feeds. Such animal feeds containing the zinc bacitracin composition of my invention may be thermally pelletized and/or processed under conditions of high temperature and moisture, with relatively little decomposition of the zinc bacitracin.

BACKGROUND

Bacitracin is an antibiotic of relatively limited human therapeutic application, namely primarily topical usage. It is an excellent feed supplement for disease prevention and treatment as well as a growth promoter, and is extensively used in its relatively stable form, zinc bacitracin, as an additive to livestock feeds, as for pigs and cattle, and to poultry feeds. Because of its limited human antibiotic utility zinc bacitracin is to be preferred as an animal feed supplement for livestock and poultry.

Zinc bacitracin has been developed as a feed supplement because of its relatively greater stability in the face of elevated temperatures and moisture than bacitracin, see U.S. Pat. No. 2,809,892 issued Oct. 15, 1957 to Francis W. Chornock. However, commercial feed grade zinc bacitracin does not have an altogether satisfactory commercial stability to temperature and moisture. Efforts to improve the stability of bacitracin compositions have included the addition of lignins to form complexes, see U.S. Pat. No. 3,035,919 issued May 22, 1962 to Jack Ziffer et al., or the addition of insoluble zinc salts such as zinc oxide, see U.S. Pat. No. 3,025,216 issued Mar. 13, 1962 to Jack Ziffer et al.

George Hines of Commercial Solvents Corporation of Terre Haute, Indiana, the manufacturer of the commercial feed supplement called "BACEFIRM", which is zinc bacitracin, has summarized the stability of this material in an article entitled "Bacifirm (Zinc Bacitracin) In Liquid Feed Supplements" which was published in the AFMA Liquid Feed Symposium Proceedings by the American Feed Manufacturers Association, 53 W. Jackson Boulevard, Chicago Ill. 60604, in 1972.

Notwithstanding extensive research, the prevention of the decomposition of zinc bacitracin, particularly when used in conjunction with animal feeds containing a variety of fats, vitamins, minerals, drugs such as coccidiocides, etc. is not well understood. While there has been an improvement in the stability of commercially available feed grade zinc bacitracin during the past decade, instability problems of this material, particularly in the presence of temperature and moisture, and in the presence of widely used animal feeds, still exist.

I have determined that admixture of zinc bacitracin with animal feeds promotes the decomposition of the zinc bacitracin, particularly when the animal feed-zinc bacitracin mixture is mechanically mixed and/or heated.

OBJECTS

This invention has as an object the provision of a zinc bacitracin composition of enhanced stability in animal feeds, namely livestock and poultry feeds, and particularly a zinc bacitracin composition which is resistant to adverse conditions of temperature, humidity, mechanical mixing, and which may be used in animal feeds as a growth promoter and therapeutic agent.

This invention has as another object the provision of a method for forming such zinc bacitracin composition having improved stability.

Other objects will appear hereinafter.

STATEMENT OF INVENTION

I have discovered that a zinc bacitracin compound with enhanced stability when mixed in feeds may be prepared by precipitating zinc bacitracin from a bacitracin fermentation broth through the addition of zinc cations in the ratios of about 0.5 to 0.7 g $Zn^{++}$/g bacitracin*. Thereafter, I regulate the pH of the fermentation broth by the application of strong alkali, such as sodium hydroxide, to a final pH of between 6.0 and 7.0. Thereafter, I remove the water from the medium by evaporation to a concentration on the order of 25 to 35 weight percent solids, such as 30 weight percent solids. I then add between about 50 to 100 weight percent based on the dry matter of a finely divided carrier, preferably calcium carbonate, and stir the slurry to obtain a uniform mixture. Thereafter, I spray dry the slurry to remove water to the order of about 1 to 5 weight percent water, as on the order of 3 weight percent**. The spray drying should be accomplished at an elevated temperature, such as the order of 300° to 450° C., and preferably 350° to 450° C., to effect very rapid drying. The resultant spray dried zinc bacitracin composition in which the zinc bacitracin is intimately associated with the carrier should be finely divided substantially solid particles of high physical strength, namely relative freedom from fracture and fines. At least 80 weight percent of the particles have a size of between 30 to 219 microns, with their shape being substantially spherical, and with their outer surfaces being relatively smooth. A major weight percentage of the particles should have a size of at least 30 to 149 microns. Generally, the specific gravity of the particles is of the order of between 0.6 and 0.7 when $CaCO_3$ is added as the carrier. The calcium carbonate content of the spray dried product should range between about 40 to 60 weight percent when the product contains 100 grams of activity per kg based on an activity of 42 I.U. per milligram. Normally, without addition of $CaCO_3$ the particles have a hollow core, and are relatively prone to destruction, as by crushing.

* Based on a bacitracin potency of 42 IU per mg.
** Where water concentration of relatively dry solids is given in this specification, the same is determined by drying the samples in vacuo below 5 mm Hg at 60° C. for 3 hours.

I have determined that the zinc bacitracin composition of my invention has an enhanced stability when admixed with animal feed compositions under conditions of high temperature, mechanical mixing, or moisture.

I do not wish to be bound by any theory or mechanism relating to the relative stability of the zinc bacitracin composition of my invention, but I believe that its stability is due to a combination of factors which include the intimate association of the zinc bacitracin and the carrier in the zinc bacitracin composition, the physical strength of the particles, the substantially spherical shape of the particles, and the relative absence of very small fines and dust.

I have done comparative drying tests in which the carrier was omitted. I have determined that it is far easier to dry zinc bacitracin in the presence of a carrier. Thus, in the absence of the carrier, the zinc bacitracin tended to stick to the walls of the spray drier. The total yield of active product is about 6 to 8% higher when the carrier is present. The flow properties of the product are far superior when the carrier is present. Thus, the product flows easier and is easier to handle. The product has a higher specific weight due to the carrier inducing the formation of substantially solid spheres having a relatively high mechanical strength.

I have determined that the yield of active product is about 10 to 15% lower when conventional drum drying is used in place of spray drying, and this I attribute mainly to thermal decomposition. The product derived from drum drying does not consist of spherical particles, and such product may be readily distinguished physically from the product of the present invention. The product from drum drying is not as stable in admixture with animal feed compositions, particularly under conditions of high temperature, mechanical mixing, and/or contact with moisture.

The carrier must be added to the concentrate prior to the spray drying. I have determined that adding finely divided calcium carbonate particles to spray dried zinc bacitracin fermentation broth, with no addition of the calcium carbonate particles prior to spray drying, does not achieve the objects of the present invention. Thus, in such instance the addition of the calcium carbonate merely functions as a diluent.

From comparative testing, such as the foregoing, I have concluded that the substantially spherical particles in which the zinc bacitracin is in intimate contact with the carrier are stable because of their relatively low surface area, and because the carrier in some fashion shields the zinc bacitracin from the adverse affects of the contact with the animal feeds and/or the adverse affects of undesirable ambient conditions, such as increased temperature, mechanical mixing and/or moisture. At the same time the activity of the zinc bacitracin in the animal feed is not adversely affected.

DETAILED DISCLOSURE OF INVENTION

The bacitracin fermentation media used by me are conventional and well described in the literature. They may contain soybean oil meal, cornstarch, cottonseed oil meal, dextrose and mineral salts.

The fermentation of the bacitracin is achieved using conventional microorganisms and conditions.

To achieve precipitation of zinc bacitracin, I follow substantially the procedure described in Chornock U.S. Pat. No. 2,809,892 and use a water-soluble zinc salt, such as for example, zinc chloride, zinc sulfate, zinc acetate, which I add to the nutrient medium in which has been cultured a bacitracin-producing strain of *Bacillus subtilis,* now designated *Bacillus licheniformis,* and which nutrient medium contains in solution bacitracin produced by the organism. Generally speaking, the bacitracin fermentation broth has a pH of about 8.2 to 8.4. Upon the addition of the water soluble zinc salt, such as a solution of zinc chloride having a concentration of 40 to 60 weight percent, such as on the order of 50 weight percent, the pH drops to a range of about 5.0 to 5.7, such as to about 5.5. The zinc bacitracin is then precipitated by the addition of a solution of strong alkali, such as about 25 weight percent sodium hydroxide, until a final pH of 6.0 to 7.0 is obtained.

I prefer to use higher concentrations of zinc than that disclosed in Chornock U.S. Pat. No. 2,809,892. I prefer to use concentrations of zinc which are in the range of 0.5 to 0.7 g $Zn^{++}$/g bacitracin in the fermentation broth. The methods for microbiological extraction and assay for the bacitracin are modified procedures of Grynne and Grove cited hereinafter in Footnote to Example 1.

The zinc bacitracin is precipitated from the solution, along with other materials which complex with zinc, such as proteins and peptides, which are inevitably present in the medium. Water is then removed by evaporation using a conventional vacuum evaporator until there is a concentration of about 25 to 35 weight percent dry matter.

When this concentration of dry matter is obtained, the finely divided carrier is then added, and the slurry is agitated by mechanical stirring to form a uniform mixture.

A variety of carriers may be utilized including calcium carbonate, calcium silicate, silica, calcium magnesium silicates, kaolin, magnesium carbonate, and other suitable carriers which may be present in animal feeds without adverse effect on the animals ingesting such feeds, and which are capable of achieving an intimate association with zinc bacitracin in the method of my invention.

The preferred carrier is calcium carbonate. The carrier should be very finely divided, and I prefer that the carrier should be sufficiently divided so that at least 80 weight percent of the particles are below 40 microns in maximum dimension. Preferably, about 85 weight percent of the carrier should be of particles having a maximum dimension of below 20 microns. Optimally, more than 50 weight percent of the carrier should have a maximum dimension of less than 10 microns.

The amount of the finely divided carrier that is added to the slurry is of the order of 50 to 100 weight percent of the dry matter in the slurry.

A carrier which I have utilized is the commercially available finely divided calcium carbonate trademarks "SJOHEST" (translation "SEAHORSE"), manufactured by Krithusbolaget i Malmo A.B. of Malmo, Sweden. This calcium carbonate is derived from organic sea deposits and has a particle size distribution of about 7 weight percent greater than 40 microns; 16 weight percent greater than 20 microns; 27 weight percent greater than 10 microns, and 44 weight percent greater than 4 microns. Its analysis is given in the following table:

| Analysis of "SEAHORSE" Calcium Carbonate | |
|---|---|
| Component | Weight Percent |
| $CaCO_3$ | 97.23 |
| $MgCO_3$ | 0.30 |
| $Fe_2O_3$ | 0.01 |
| $Al_2O_3$ | 0.07 |
| $SiO_2$ | 0.30 |
| Acid Insolubles | 0.79 |
| Organic Matter | <0.36 |
| Water Soluble Matter | 0.25 |
| Water | 0.07 |
| $MnO_2$ | 120 ppm |

The density of "SEAHORSE" is 0.8 (kg/l); the surface area is about 2 square meters per gram BET, pH is about 9.0 to 9.2, the hardness is about 3(Mho), and the crystal structure is cryptocrystalline.

The uniform mixture of the concentrated zinc bacitracin fermentation broth and carrier is then spray dried. Conventional spray drying equipment and techniques may be used to achieve a zinc bacitracin composition of the present invention. However, I prefer to use relatively high inlet temperatures of air, such as on the order of 300° to 450° C., preferably 350° C. to 450° C., to achieve rapid drying. When rapid drying is achieved, there is a minimal amount of decomposition of the zinc bacitracin, since the relatively dry product can withstand high temperatures and the water is removed very rapidly.

While as above indicated I prefer to dry to a water concentration of the order of 1 to 5 weight percent, drying to other moisture levels may be accomplished depending upon existing equipment facilities.

Typically, more than 80 weight percent of the dried product particles have a dimension of between 30 to 219 microns, and preferably more than a major weight percentage of the particles should have a size of at least 30 to 149 microns.

After drying, the zinc bacitracin composition may be blended with a diluent to standardize its potency, such as any of the conventional diluents like dried distiller's solubles, corn gluten feed, or soy bean meal, and then blended with conventional animal feeds, such as poultry, swine or cattle feed.

The combination of the zinc bacitracin composition of the present invention with animal feeds possesses superior stability. The zinc bacitracin-animal feed mixture may be treated at elevated temperatures, and stored with a smaller loss of potency than is achieved with existing mixtures of commercially obtainable zinc bacitracin and animal feeds.

The nature of the culture medium and the proteins and peptides precipitated with the zinc bacitracin does not appear to be significant in affecting the parameters and process variables of my process, although these materials may affect the stability of the zinc bacitracin composition of my invention in some manner not understood by me. The proteins and peptides of the culture medium may complex with the zinc cations, and with the zinc bacitracin as in conventional zinc bacitracin mixtures used in animal feeds. Because of the presence of these other zinc complexing materials it is not possible to specify the amount of zinc that is complexed with the bacitracin in molar amounts.

The control of pH with strong alkali, such as sodium hydroxide, should be such that the precipitate containing the zinc bacitracin should be completed at a pH of between 6.0 to 7.0. The time of adjustment, rate of agitation, and temperature of the solution during precipitation do not appear to be significant variables as long as a homogeneous mass containing the zinc bacitracin is obtained.

EXAMPLES

The following examples are illustrative of the composition and process of the present invention. The examples are to be deemed as illustrative and are not intended to delimit the particular proportions, materials, and other parameters which are set forth. Moreover, the specification and the examples are addressed to one having skill in the art and it is not intended that the same be distorted beyond reasonable limits.

The following experiments illustrate the effect of the concentration of zinc on the stability of the zinc bacitracin in the fermentation broth.

EXAMPLE 1

Zinc chloride in various amounts is added to a fermentation broth with a pH of 8.3 containing 700 IU/ml* under agitation (16.6 g bacitracin/l). After adjusting the pH to 6.5 to 6.8 the samples are heated in closed glass flasks at 90° C. for 4 hours and cooled at room temperature.

| $Zn^{++}$ g/l fermentation broth | Bac.* g/l fermentation broth | g $Zn^{++}$ added to 100 g bac. | % loss of bac. |
|---|---|---|---|
| 0 | 16.6 | 0 | 52 |
| 2.4 | 16.6 | 14.5 | 40 |
| 4.8 | 16.6 | 29.0 | 35 |
| 7.2 | 16.6 | 43.0 | 35 |
| 9.6 | 16.6 | 58.0 | 26 |

*Based on a potency of 42 IU per mg. The extraction of the zinc bacitracin for potency measurement was affected by the procedure of Grynne set forth in the article entitled "An Improved Method For The Determination Of Bacitracin In Animal Feeds" in the May 1971 Analyst, Vol. 96, pages 338-342 at pages 338 and 339 by B. Grynne, with the modification that all samples were treated with acetone. The zinc bacitracin in the extracts was determined microbiologically according to the procedure in "Assay Methods Of Antibiotics", by D.C. Grove and W.A. Randall, Medical Encyclopedia Inc. (1965) pages 76 through 78, with the modification that the seed agar layer was omitted. A 3-pont assay with the concentrations 0.01 to 0.05 and 0.025 I.U./ml for standard and sample was used.

EXAMPLE 2

The experiment was carried out with a fermentation broth containing 350 IU/ml (8.3 g bacitracin/l). The procedure was analogous to that described in Example 1.

| $Zn^{++}$ g/l fermentation broth | Bac. g/l fermentation broth | g $Zn^{++}$ added to 100 g bac. | % loss of bac. |
|---|---|---|---|
| 0 | 8.3 | 0 | 56 |
| 4.2 | 8.3 | 51.0 | 35 |
| 4.8 | 8.3 | 58.0 | 27 |
| 5.4 | 8.3 | 65.0 | 26 |

EXAMPLE 3

The experiment was carried out with a fermentation broth containing 420 IU/ml (10 g bacitracin/l). The procedure was analogous to that described in Example 1.

| $Zn^{++}$ g/l fermentation broth | Bac. g/l fermentation broth | g $Zn^{++}$ added to 100 g bac. | % loss of bac. |
|---|---|---|---|
| 3.6 | 10.0 | 36.0 | 34 |
| 4.8 | 10.0 | 48.0 | 35 |
| 6.0 | 10.0 | 60.0 | 25 |
| 7.2 | 10.0 | 72.0 | 26 |

EXAMPLE 4

The experiment was carried out with a fermentation broth containing 630 IU/ml (15 g bacitracin/l). The procedure was analogous to that described in Example 1.

| $Zn^{++}$ g/l fermentation broth | Bac. g/l fermentation broth | g $Zn^{++}$ added to 100 g bac. | % loss of bac. |
|---|---|---|---|
| 0 | 15.0 | 0 | 56 |
| 7.2 | 15.0 | 48.0 | 40 |
| 8.4 | 15.0 | 56.0 | 40 |
| 9.6 | 15.0 | 64.0 | 27 |
| 10.8 | 15.0 | 72.0 | 26 |

The following experiments reveal the spray drying of the zinc bacitracin:

EXAMPLE 5

Zinc chloride in the amount of 0.5 g $Zn^{++}$/g bacitracin was added to a fermentation broth, thereafter the pH was adjusted to 6.8. By evaporation the broth was concentrated and spray dried at air inlet temperatures of 350° C. to 400° C. and air outlet temperatures of 115° to 120° C. The recovery of the spray drying step in four individual experiments was as follows:

| Experiment | Temp. ° C. | Dry matter of concentrate, % | % recovery |
|---|---|---|---|
| 1 | 350 | 28 | 94.5 |
| 2 | 350 | 28 | 94.5 |
| 3 | 425 | 25 | 86.8 |
| 4 | 370 | 24 | 93.2 |

Mean recovery: 92.3%

EXAMPLE 6

Zinc chloride in the amount of 0.50 g $Zn^{++}$/g bacitracin was added to the fermentation broth, thereafter the pH was adjusted to 6.7.

By evaporation the broth was concentrated. Based on its dry matter 50% resp. 100% "SEAHORSE" $CaCO_3$ was added. Subsequently spray drying was carried out at air inlet temperatures of 350° to 400° C and air outlet temperatures of 115° to 120° C. The recovery of the spray drying step in four individual experiments was as follows:

| Experiment | Wt. % $CaCO_3$ | Temp ° C. | Dry matter of concentrate, % | % recovery |
|---|---|---|---|---|
| 5 | 50 | 350 | 28 | 101.5 |
| 6 | 50 | 400 | 28 | 102.5 |
| 7 | 50 | 400 | 25 | 98.2 |
| 8 | 100 | 420 | 25 | 96.1 |

Mean recovery: 99.6%

Physical data of spray dried products.

|  |  | With $CaCO_3$ | Without $CaCO_3$ |
|---|---|---|---|
| Particle size: | above 219 μ | approx. 10% | approx. 10% |
|  | 30 – 219 μ | approx. 80% | approx. 80% |
|  | 30 – 149 μ | approx. 60% | approx. 60% |
|  | below 30 μ | approx. 10% | approx. 10% |
| Moisture |  | 1 – 3% | 3 – 5% |
| Bulk density |  | 0.6 – 0.7 g/cm³ | 0.3 – 0.35 g/cm³ |

The following experiments demonstrate the stability of the zinc bacitracin of the present invention in corn and feed mixtures:

EXAMPLE 7

The experiments were carried out in a feed mixer of total volume 54 l, using charges of 25 kgs corn. The mixer was provided with a steam jacket and prior to the addition of 200 ppm zinc bacitracin, the corn was preheated to 95° C. During continuous mixing samples were drawn after 1, 4 and 10 minutes. The samples were cooled by air before being analyzed.

In order to study their storage stability, samples were kept in paper bags at room temperature for 3 months before being analyzed.

The results are set forth in Table 1.

TABLE 1*

| Conditioning time | Maize Corn loss in activity Control product[1] | during conditioning Modified product[2] |
|---|---|---|
| 1 min. | 0%[3] | 0%[3] |
| 4 min. | −11.7% | +4.5% |
| 10 min. | −29.9% | −4.5% |

*With reference to Tables 1, 2 and 3:
[1]Control product: drum dried product.
[2]Modified product: spray dried product with addition of $CaCO_3$ and 0.5 g $Zn^{++}$/g bacitracin before drying step.
[3]The analytical value of the 1 min. conditioned, not stored, samples are used as reference (100% activity, i.e. 0% loss) for calculating conditioning and total loss.

EXAMPLE 8

The experiments were carried out in swine feed using the same conditions as described in Example 7. Recipe of swine feed:

| Components | Content % |
|---|---|
| Barley | 38.00 |
| Ground corn | 12.00 |
| Ground soybean, extr. | 13.20 |
| Protein conc. for swines | 10.00 |
| Rye bran | 8.75 |
| Tapioca roots | 8.00 |
| Luzerne meal | 5.00 |
| Corn gluten feed | 3.00 |
| Fat | 1.00 |
| Mineral mixture | 1.00 |
| Vitamin premix | 0.05 |
|  | 100.00 |

The results of the analyses on the swine feed are set forth in Table 2:

TABLE 2

SWINE FEED

| Conditioning time | Loss in activity during conditioning Control product[1] | Loss in activity during conditioning Modified product[2] | Loss during 3 months storage Control product | Loss during 3 months storage Modified Product | Total loss Control Product | Total loss Modified Product |
|---|---|---|---|---|---|---|
| 1 min. | 0%[3] | 0%[3] | −7.6% | −6.7% | −7.6% | −6.7% |
| 4 min. | −6% | −4.7% | Not analyzed | Not Analyzed | Not Analyzed | Not Analyzed |
| 10 min. | −14.3% | −19.8% | −7.0% | +8.0% | −21.2% | −13.4% |

EXAMPLE 9

The experiments were carried out in laying hen feed using the same conditions as described in Example 7. Recipe of laying hen feed:

| Components | Content % |
|---|---|
| Ground corn | 40.00 |
| Ground wheat | 5.00 |
| Ground soybean | 15.00 |
| Corn gluten feed | 11.75 |
| Wheat bran | 11.00 |
| Meat and bone meal | 5.50 |
| Luzerne meal | 3.50 |
| Fodder chalk | 3.00 |
| Fish meal | 3.00 |
| Mineral mixture | 1.00 |
| Fats | 1.00 |
| Vitamin premix | 0.25 |
|  | 100.00 |

The results of the analyses are set forth in Table 3:

TABLE 3

| | LAYING HEN FEED | | | | | |
|---|---|---|---|---|---|---|
| | Loss in activity | | Loss during | | | |
| Conditioning Time | Control Product[1] | Modified Product[2] | Control Product | Modified Product | Control Product | Modified Product |
| 1 min. | 0%[3] | 0%[3] | −7.8% | −5.8% | −7.8% | −5.8% |
| 4 min. | −4.6% | +4.7% | −29.0% | −28.0% | −31% | −24.6% |
| 10 min. | −20.9% | −11.4% | −36.2% | −27.7% | −50% | −32.7% |

By virtue of the improved stability against heat, mechanical mixing and moisture possessed by the zinc bacitracin compositions of the present invention, animal feeds containing such zinc bacitracin compositions have superior properties in terms of thermal treatments. Prior to thermally pelletizing animal feeds, it is conventional to condition such animal feeds by mechanical mixing of the feeds at a raised temperature, such as of the order of 75° to 85° C. Subsequent thermal pelletization of animal feeds containing the zinc bacitracin compositions of the present invention may result in superior maintenance of the potency of the zinc bacitracin.

The shelf life potency of animal feeds containing the zinc bacitracin compositions of the present invention is superior to those of existing commercial animal feeds containing zinc bacitracin.

The present invention may be embodied in other specific forms without departing from the spirit or essential attributes thereof and, accordingly, reference should be made to the appended claims, rather than to the foregoing specification as indicating the scope of the invention.

I claim:

1. A process for the production of a zinc bacitracin composition with enhanced stability suitable for use in animal feeds which includes precipitating zinc bacitracin from a fermentation broth, adjusting the pH of the fermentation broth with alkali to within the range of 6.0 to 7.0, removing water by evaporation from the fermentation broth without filtration to yield a slurry containing between about 25 to 35 weight percent dry matter, adding about 50 to 100 weight percent based on the dry matter of the slurry of a finely divided carrier in which 80 weight percent of the particles making up the carrier have a dimension of below 40 microns, blending the mixture to uniformly disperse the carrier particles, spray drying such uniform dispersion at a temperature of between about 300° to 450° C. so that the water is rapidly removed to produce finely divided substantially spherical particles containing the zinc bacitracin in intimate contact with the carrier.

2. A process in accordance with claim 1 in which 80 weight percent of the spherical particles have a dimension of between 30 to 219 microns.

3. A process in accordance with claim 1 in which the carrier is calcium carbonate.

4. A process in accordance with claim 3 in which a major weight percent of the spherical particles have a dimension of between 30 to 149 microns, and are substantially solid.

5. A process in accordance with claim 1 in which the amount of zinc cation that is added to the bacitracin-containing fermentation broth to precipitate and stabilize the zinc bacitracin is between 0.5 to 0.7 g $Zn^{++}$/g bacitracin in the fermentation broth.

6. A process in accordance with claim 1 in which about 85 weight percent of the finely divided carrier particles have a dimension of below 20 microns.

7. A process in accordance with claim 1 in which the spherical particles contain between about 1 to 5 weight percent water.

8. A process in accordance with claim 1 in which the spray drying is effected at a temperature of between 350° to 450° C.

9. An animal feed additive made in accordance with the process of claim 1.

10. An animal feed additive made in accordance with the process of claim 2.

11. An animal feed additive made in accordance with the process of claim 3.

12. An animal feed additive made in accordance with the process of claim 4.

13. An animal feed additive made in accordance with the process of claim 5.

14. An animal feed additive made in accordance with the process of claim 6.

15. An animal feed additive made in accordance with the process of claim 7.

16. An animal feed additive made in accordance with the process of claim 8.

* * * * *